United States Patent
Braune

(10) Patent No.: US 6,174,970 B1
(45) Date of Patent: *Jan. 16, 2001

(54) METHOD OF REPROCESSING RESIDUES CONTAINING DIHYDROXY COMPOUNDS

(75) Inventor: Peter Braune, Erbes-Büdesheim (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/125,064

(22) PCT Filed: Mar. 4, 1997

(86) PCT No.: PCT/EP97/01081

§ 371 Date: Aug. 7, 1998

§ 102(e) Date: Aug. 7, 1998

(87) PCT Pub. No.: WO97/32915

PCT Pub. Date: Sep. 12, 1997

(30) Foreign Application Priority Data

Mar. 6, 1996 (DE) ................................. 196 08 614

(51) Int. Cl.$^7$ ................................. C08F 2/00; C08G 65/00
(52) U.S. Cl. ................................. 526/67; 526/65; 526/66; 526/68; 528/272; 528/48; 528/495; 528/501; 528/503
(58) Field of Search ................................. 526/65, 66, 67, 526/68; 528/272, 488, 495, 501, 503

(56) References Cited

U.S. PATENT DOCUMENTS

| 3,852,164 | 12/1974 | Chow et al. | 203/91 |
| 4,154,970 | * 5/1979 | Beer et al. | 568/868 |
| 5,561,218 | * 10/1996 | Braune | 528/491 |
| 5,789,500 | * 8/1998 | Braune | 526/67 |

OTHER PUBLICATIONS

*Textilindustrie*, 40 (1992), pp. 1058–1062.
*Ullmann's Enz. der tech. Chem.*, 4 Aufl., vol. 19, pp. 61–88.

* cited by examiner

*Primary Examiner*—Samuel A. Acquah
(74) *Attorney, Agent, or Firm*—Keil & Weinkauf

(57) ABSTRACT

A process for working up residues containing dihydroxy compounds resulting from the preparation of polyesters, where (1) in a first stage there is esterification or transesterification of a dicarboxylic acid or esters thereof or ester-forming derivatives with a molar excess of a dihydroxy compound, (2) in at least one second stage there is polycondensation of the esterification product obtained in (1), (3) the vapors (a) and (b) resulting from the reactions in (1) and (2) respectively are subjected to a treatment to recover the starting materials, wherein the treatment to recover the starting materials is carried out in the presence of an alkali metal or alkaline earth metal compound in an amount of from 0.5 to 10% by weight, calculated as alkali metal or alkaline earth metal, based on the solids content of the vapors.

21 Claims, 3 Drawing Sheets

METHOD OF REPROCESSING RESIDUES CONTAINING DIHYDROXY COMPOUNDS

Figure 1:
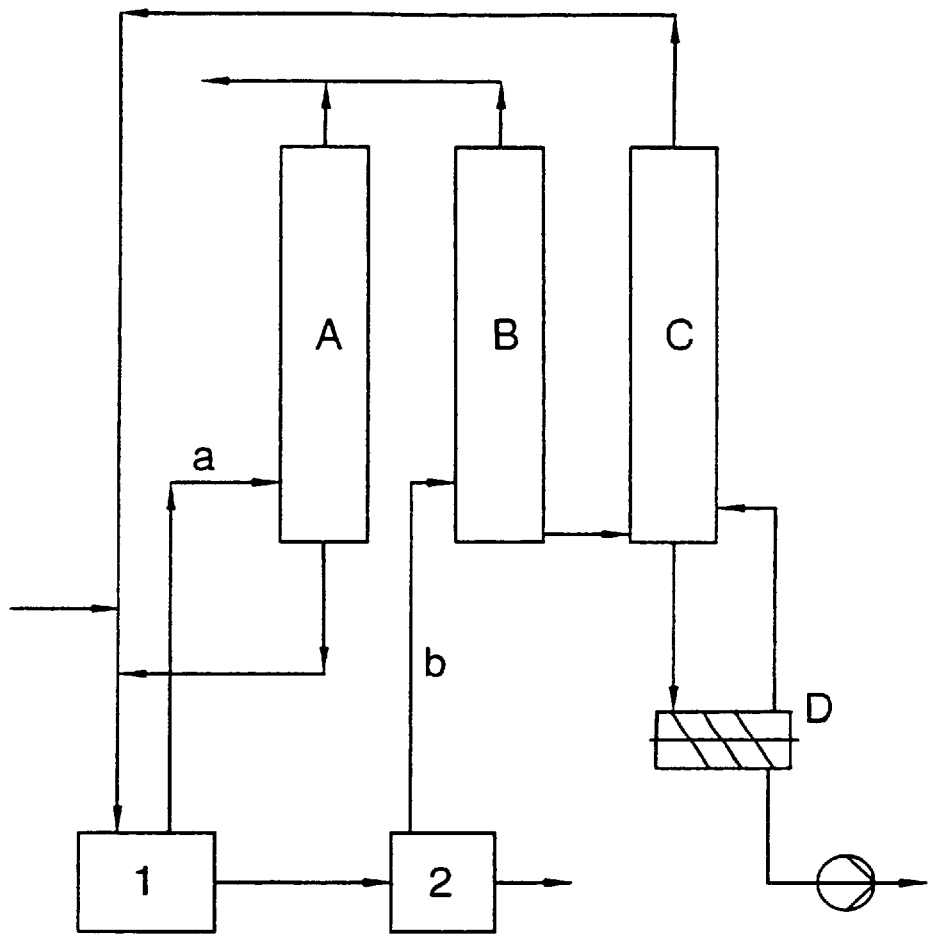

The present invention relates to a process for working up residues containing dihydroxy compounds resulting from the preparation of polyesters, where
(1) in a first stage there is esterification or transesterification of a dicarboxylic acid or esters thereof or ester-forming derivatives with a molar excess of a dihydroxy compound,
(2) in at least one second stage there is polycondensation of the esterification product obtained in (1),
(3) the vapors (a) and (b) resulting from the reactions in (1) and (2) respectively are subjected to a treatment to recover the starting materials.

Polyesters, especially polyalkylene terephthalates, are prepared on a large scale in transesterification/polycondensation processes where an esterification or transesterification is carried out in a first stage, and the actual polycondensation is carried out in at least one further stage (cf. Chemiefasern/Textilindustrie 40 (1992), 1058–1062 and Ullmann's Enzyklopädieder technischen Chemie, 4th Edition, Volume 19, pages 61–88).

This process will be briefly explained taking the example of the preparation of polybutylene terephthalate from terephthalic acid and 1,4-butanediol.

In a first reaction chamber, terephthalic acid is esterified with a molar excess, preferably 50–120 mol %, in particular 70–100 mol %, of 1,4-butanediol, and the esterified compound is subjected in further steps to the actual polycondensation. The vapors resulting from the esterification are transferred into a column in which the low-boiling components THF/water are removed as distillate, and a bottom product which, besides excess 1,4-butanediol, also contains small amounts of oligomers, polymers and terephthalic acid is obtained.

The esterification product is subsequently polycondensed, expediently in at least two stages, called the precondensation and postcondensation, in continuous processes.

For economic reasons, it is desirable in this connection that as much as possible of the resulting reaction products and dihydroxy compounds present in excess are treated further in order, for example, to recover the 1,4-butanediol and generate as little waste as possible.

A process for treating the vapors from the polycondensation is proposed in DE-A 19509957.5 which is not a prior publication.

DE-A 43 33 929 discloses a process for recovering the starting materials, where a distillation residue consisting of dihydroxy-containing compounds (called "Hex") is metered into the column to simplify manipulation of the bottom products which are mostly extremely viscous.

The disadvantage of this process is that this residue usually derives from the distillation of butanediol or hexanediol and is thus not available everywhere.

Since the vapors contain oligomeric and polymeric esters, in addition to the starting materials and byproducts, the pH of the vapors is below 7 owing to the content of carboxyl end groups. In addition, renewed fragmentation takes place during recovery, resulting in new carboxyl end groups besides those already present. For these reasons, treatment of the vapors is very costly because it is necessary to employ corrosion-resistant stainless steel containers.

During the treatment and preparation of polyesters there is considerable formation of, for example, THF as byproduct (when 1,4-butanediol is the starting material). Since this side reaction is catalyzed by acids, there are also considerable losses of 1,4-butanediol due to THF formation on recovery by distillation.

It is an object of the present invention to remedy the disadvantages described above and to improve the working up of the vapors so that most of the dihydroxy compounds present therein can be recovered as economically as possible. It is intended at the same time that the quality of the polyester product be maintained.

We have found that this object is achieved by carrying out the treatment to recover the starting materials in the presence of an alkali metal or alkaline earth metal compound in an amount of from 0.5 to 10% by weight, calculated as alkali metal or alkaline earth metal, based on the solids content of the vapors.

The addition, according to the invention, of alkali metal or alkaline earth metal compounds in the treatment of the vapors results in a basic buffering of the vapors so that corrosion of the containers is no longer possible. This makes it possible to employ considerably lower-cost ordinary steel containers for these purposes. In addition, the formation of byproducts, eg. THF, is considerably reduced.

Moreover, at a pH of 7 or above for the vapors, shorter fragments, eg. of the polymeric residues, are present so that, on the one hand, they can be dispersed more easily in the dihydroxy compound, ie. the resulting distillation residue is easier to handle because it has a lower viscosity. On the other hand, the columns can be operated for considerably longer without cleaning (longer service lives) and the solid residues can be removed more easily from the column on cleaning, eg. with water.

In a particular embodiment of the invention, further butanediol, for example, can be recovered in the evaporation apparatus following the distillation treatment, and this working up is independent of the availability of the residue containing dihydroxy compounds (HEX).

In the process according to the invention, from 0.5 to 10, preferably 1 to 8 and, in particular, 2.5 to 6, % by weight, calculated as alkali metal or alkaline earth metal, based on the solids contents of the vapors, are added preferably to the bottom product from columns A, B or C in the treatment of the vapors.

Suitable in principle are inorganic and organic compounds of the alkali metals, preferably of Li, Na, K, particularly preferably Na compounds.

Suitable inorganic compounds of the alkaline earth or alkali metals, preferably of sodium, are, for example, the corresponding silicates, phosphates, phosphites, sulfates or, preferably, carbonates, bicarbonates and hydroxides.

The organic compounds of the alkaline earth or alkali metals, preferably of sodium, include the corresponding salts of (cyclo)aliphatic, araliphatic or aromatic carboxylic acids having, preferably, up to 30 carbon atoms and, preferably, 1 to 4 carboxyl groups. Examples thereof are: alkali metal salts of formic acid, acetic acid, propionic acid, butyric acid, isobutyric acid, caprylic acid, stearic acid, cyclohexanecarboxylic acid, succinic acid, adipic acid, suberic acid, 1,10-decanedicaroxylic acid, 1,4-cyclohexanedicarboxylic acid, terephthalic acid, 1,2,3-propanetricarboxylic acid, 1,3,5-cyclohexanetricarboxylic acid, trimellitic acid, 1,2,3,4-cyclopentanetetracarboxylic acid, pyromellitic acid, benzoic acid, substituted benzoic acids, dimer acid and trimer acids, and neutral or partially neutralized montan wax salts or montan wax ester salts (montanates). Salts with other types of acid residues, such as alkali metal paraffin-, olefin- and arylsulfonates or else phenolates, and alcoholates, such as methanolates, ethanolates, glycolates, can also be employed according to the invention. Sodium carbonate, sodium bicarbonate, sodium hydroxide, sodium salts of mono- and polycarboxylic acids, in particular aliphatic mono- and polycarboxylic acids, preferably those having 2 to 18 carbon atoms, in particular having 2 to 6 carbon atoms, and up to four, preferably up to two, carboxyl groups, and sodium alcoholates having, preferably, 2 to 15, in particular 2 to 8, carbon atoms are preferably used. Examples of particularly preferred representatives are sodium acetate, sodium propionate, sodium butyrate, sodium oxalate, sodium mallonate, sodium succinate, sodium methanolate, sodium ethanolate, sodium glycolate. Sodium methanolate is very particularly preferred and is particularly advantageously employed in an amount of from 2.5 to 6% by weight, calculated as Na, based on the solids content of the vapors. It is also possible to employ mixtures of various alkaline earth or alkali metal compounds.

The alkaline earth or alkali metal or compound thereof can be added in at least one column A, B or C depending on the method of working up. It is, of course, also possible to distribute the addition over all the columns, in which case it is preferred to meter equal amounts into each column.

The process according to the invention will be illustrated hereinafter by the example once again of the preparation of polybutylene terephthalate with reference to the figures; however, it is emphasized once again that it is also suitable correspondingly for preparing other polyesters known to the skilled worker.

Firstly, terephthalic acid and 1,4-butanediol (the latter in an excess of from 150 to 220 mol %, preferably 70 to 100 mol %) are reacted together in a conventional way at from 150 to 220° C. under from 0.7 go 2.0 bar for from 150 to 300, preferably 200 to 280, minutes, during which esterification takes place and resulting THF (tetrahydrofuran) is transferred together with excess butanediol (BD) and small amounts of oligomeric and polymeric compounds, and residual amounts of terephthalic acid, with the vapors (a) into a column A. The feed point is preferably in the middle or in the lower part of the column.

Stage (1) of the process is depicted in the figures as one process step. Stage (1) is preferably divided into at least four process steps, these being composed of a mixing reactor for solvent, catalyst etc. and at least three stirred reactors.

The esterification product from stage (1) of the process is polycondensed in at least one second stage (2). This polycondensation is carried out in a conventional way at from 240° C. to 270° C. under from 0.3 to 200 mbar for from 60 to 200, preferably 70 to 180, minutes. A particularly preferred embodiment of stage (2) is division into two process steps, carrying out firstly a precondensation and then a postcondensation.

FIG. 1 depicts a preferred embodiment for recovering the starting materials, in which the vapors (a) resulting in stage (1) are transferred into at least one column A, and the low-boiling components of the vapors (a) are removed as distillate, and the bottom product is returned to stage (1), and the vapors (b) resulting in stage (2) are transferred into at least one column B, and the low-boiling components are removed as distillate, and the bottom product is discharged from column B and subsequently subjected in at least one column C to a further treatment to recover the dihydroxy compound.

Figure 2:
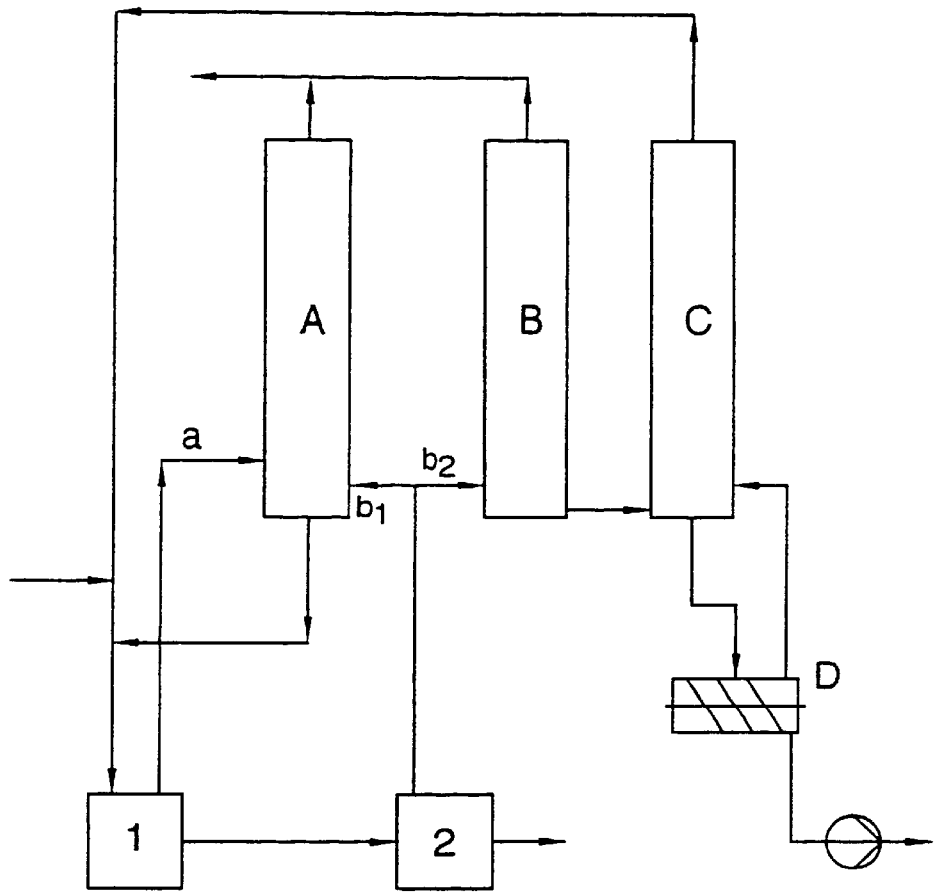

FIG. 2 depicts a further preferred process for working up the vapors, in which the vapors (a) resulting in stage (1) and part of the vapors (b$_1$) from stage (2) of the process are combined in at least one column A, and the low-boiling components of the vapors are removed as distillate in column A, and the bottom product which mainly contains the excess dihydroxy compounds, and oligomeric and polymeric reaction products, is returned to stage (1), and the other part of the vapors (b$_2$) from stage (2) of the process is transferred into at least one column B, and the low-boiling components of the vapors are removed as distillate, and the bottom product is discharged from column B and subsequently subjected in at least one column C to a further treatment to recover the dihydroxy compound.

It is possible by dividing the vapors from the polycondensation, with preferably the vapors (b$_1$) deriving from the precondensation and the vapors (b$_2$) deriving from the postcondensation, in a technically simple manner to return the excess diol to the esterification. This makes the process more economic and less costly, while the quality of the polyester product is maintained.

Figure 3:
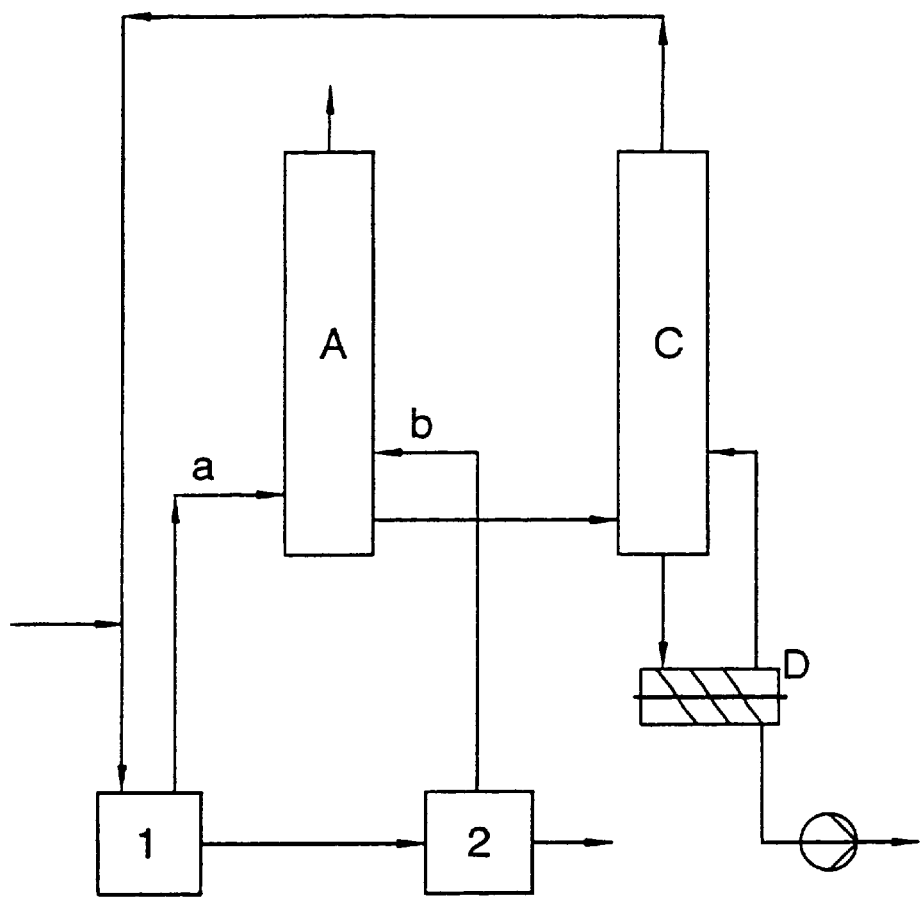

FIG. 3 depicts another preferred embodiment of the process, in which the vapors (a) and (b) resulting in stages (1) and (2) are transferred into at least one column A, and the low-boiling components are removed as distillate, and subsequently the bottom product is discharged from column A and subjected in at least one column C to a further treatment to recover the dihydroxy compound.

The low-boiling THF/water is removed as distillate in column A or B of the process according to the invention, and these low-boiling components are subsequently subjected to a recovery of the starting materials (separation of THF from water).

In the case of the preparation of polyethylene terephthalate, the low-boiling components essentially consist of water or methanol with acetaldehyde; in the preparation of PBT starting from dimethyl terephthalate they consist of methanol and THF. The bottom product, which mainly contains the excess dihydroxy compounds, is then returned to stage (1). Depending on the size of the system, columns A to C can be divided into a plurality of columns A$_1$, A$_2$ to A$_n$ or B$_1$, B$_2$ to B$_n$ and C$_1$, C$_2$ to C$_n$.

In the preferred embodiments depicted in FIGS. 2 and 3, the vapors are worked up in such a way that the vapors from stage (2), which mainly contain THF, water, excess butanediol and somewhat larger amounts of oligomeric and polymeric compounds than in the vapors from stage (1), and residual amounts of terephthalic acid, are transferred either partly into columns A and B or completely into a column A, in which case the vapors from stage (1) of the process are already present in column A.

In the preferred embodiment in FIG. 1, the working up takes place separately and the vapors (b) are transferred into a column B.

The feed point is preferably in the middle or in the lower part of the columns. The manner of dividing up these parts is self-evident because the dividing up depends on the capacity of the columns and the quality of the required starting materials in the esterification.

The low-boiling components of the vapors are removed as distillate, and the bottom product from column A and/or B, depending on the procedure, is discharged. The bottom product is subsequently subjected to a further treatment to recover the dihydroxy compound. This is done by discharging the bottom product from column A or B, depending on the procedure, into a column C, with or without removal of the solids.

A liquid residue containing dihydroxy compounds ("Hex"), resulting, for example, from the distillation of 1,4-butanediol or 1,6-hexanediol is preferably introduced into column C in parallel. There is no particular restriction per se on the composition of the residue as long as it is liquid and contains no compounds interfering with the separation in the column. This is usually the case with residues from the distillation of butanediol or hexanediol.

The feed point is preferably in the middle or in the lower part of the column, and the feed rate is generally from 0.03 to 5 kg per kg of bottom products transferred into the column, preferably from 0.04 to 0.1 kg/kg.

The addition of this residue containing dihydroxy compounds results in the bottom product in column C remaining liquid or transportable, and it is therefore possible to obtain in a technically simple manner the dihydroxy compound as distillate and a bottom product in this column, which is once again liquid or transportable and can easily be delivered for incineration.

The dihydroxy compound is subsequently returned from column C to the esterification (stage 1).

In a particularly preferred embodiment of the process according to the invention, the bottom product from column C is discharged into an evaporation apparatus D, and the dihydroxy compound is removed and returned to column C, and the remaining residue is discharged from D.

This preferred embodiment results in further 1,4-butanediol, for example, being recovered and makes it possible to work up the residue in a simple and economic manner without adding a distillation residue. Another advantage of this procedure is that it is unnecessary for removal of the dihydroxy compound in column C to be complete, and the residue is not so viscous and thus can still be handled.

The feed point of the recovered butanediol is preferably in the lower part of column C, in particular above the vapor space of the bottom of column C.

Examples of suitable evaporation apparatus D are special columns, stirred evaporators, extruders, self-cleaning evaporators and tray evaporators.

The temperature of the evaporation apparatus is preferably above the melting point of the remaining residue. This depends on the solids content and the nature of the residue. The temperature for the residue from the preparation of polybutylene terephthalate is normally 180 to 250° C., preferably 190 to 230° C., and for residues from the preparation of polyethylene terephthalate is generally from 180 to 280° C., preferably 190 to 265° C.

If the bottom product is concentrated in apparatus D only to a solids content of from 30 to 70%, based on the discharged bottom product, lower temperatures from 150 to 220° C. in apparatus D are likewise suitable.

It is possible via the process according to the invention to recover the starting materials such as butanediol to a considerable extent in a simple and low-cost manner. At the same time, the content of byproducts such as THF is drastically reduced.

EXAMPLE 1 (FIG. 2)

Stage 1

35.2 mol of terephthalic acid (TPA) and 82.7 mol of 1,4-butanediol (BD) were reacted in a 3-stage esterification cascade at 210–220° C. under 2 bar absolute. 30 ppm Ti based on polybutylene terephthalate (PBT) were added as tetrabutyl orthotitanate (TBOT) as catalyst (residence time $\tau$=205–260 min in total).

The reaction product was transferred with a conversion of at least 95% into stage 2. At the start of the precondensation, 50 ppm Ti based on PBT were added as TBOT:

$\tau$=30–40 min,

T=240–290° C.,

P=0.8 bar initially up to 25 mbar.

After the precondensation in stage 2, the product was transferred with a conversion of at least 98.5% into the postcondensation of stage 2. At the start of the postcondensation, 30 ppm Ti based on PBT were added as TBOT.

$\tau$=90–140 min,

T=245–265° C.,

P=0.5 to 2,0 mbar.

The PBT product was then discharged as a melt with a viscosity $\eta$ (intrinsic) of 0.9–1.3 and was granulated.

The excess molar BD was worked up as depicted in principle in FIG. 2 under the various conditions shown in the table.

Procedure for BD Recovery:

The vapors from stage (1) were transferred as stream (a) (see Tab. to FIG. 2) at 210–220° C. under 2 bar absolute into column A. Water and THF were removed as distillate. The butanediol was returned to stage (1). The butanediol present in the vapors from stage (2) (stream $b_1+b_2$) was fed as liquid with all the vapors from this stage into columns A and B. This entailed the pre- and postcondensation streams being divided so that the vapors from the postcondensation in stage (2) and part of the vapors from the precondensation in stage (2) being fed as liquid into column B, while the other part of the vapors from the precondensation in stage (2) was fed into column A.

Column A was operated under the same pressure as the esterification in stage (1). Columns/apparatus B, C, D were operated under a pressure $\leq 1$ bar absolute. THF and water were taken off as distillate from column B, and the butanediol present in the bottom product from column B was fed into column C. Butanediol was removed as distillate from column C. The bottom product from column C was fed into apparatus D where the butanediol was removed quantitatively as vapor and returned to the vapor space over the bottom of column C.

With the procedure of Example 1, 0.1 mol of PBT was discharged per 35.2 mol of TPA from apparatus D. Without apparatus D, the same amount of solid was discharged from the bottom of column C.

The BD losses for the various working-up variants of Example 1 are listed in Table 1 for FIG. 2.

Working-up variants 1.1. to 1.5. therein were carried out in the following ways:

1.1. The distillation residue "Hex" was fed into column B in a total amount of 3.4 kg/kg of solids present in vapors $b_2$ (for comparison as disclosed in DE-A 43 33 929).

1.2. Sodium methanolate (30% strength in methanol) was fed into column B in an amount of 0.05 kg Na/kg of solids present in vapors $b_2$.

In addition, "Hex" was fed in as in 1.1.

1.3. Na methanolate was fed in as in 1.2. but without "Hex". The bottom product from column C was fed into evaporation apparatus D. The BD was returned as vapor to the vapor space above the bottom of column C. The solid was discharged from D as melt at 235° C.

1.4. Neither "Hex" nor Na methanolate was fed in (for comparison).

1.5. As in 4 but without apparatus D (for comparison).

TABLE 1

Example 1

| Working-up variant | I THF Reaction | II THF Distill. | III BD Discharge C or D | IV $b_2$ back | IV $b_2$ in | V $b_1$ back | V $b_1$ in | VI a | VII BD for working up $a + b_1 + b_2$ | VIII BD loss in the working up (THF + discharge) | IX Solid discharge C or D | X Service life Heat exchangers Columns Pipelines (in days) |
|---|---|---|---|---|---|---|---|---|---|---|---|---|
| 1.1. *) | 7.0 | 0.5 | 0.6 | 7.5 | 8.6 | 17.9 | 17.9 | 14.1 | 40.6 | 1.1 | 0.1 | 15–20 |
| 1.2. | 7.0 | <0.1 | 0.3 | 8.3 | 8.6 | 17.9 | 17.9 | 14.1 | 40.6 | 0.3 | 0.1 | 30–200 |
| 1.3. | 7.0 | <0.1 | <0.1 | 8.6 | 8.6 | 17.9 | 17.9 | 14.1 | 40.6 | <0.1 | 0.1 | 30–150 |
| 1.4. *) | 7.0 | 0.75 | 0.3 | 7.55 | 8.6 | 17.9 | 17.9 | 14.1 | 40.6 | 1.05 | 0.1 | 7–10 |
| 1.5. *) | 7.0 | 0.75 | 1.2 | 6.65 | 8.6 | 17.9 | 17.9 | 14.1 | 40.6 | 1.95 | 0.1 | 7–10 |

I—IX: all data in mol
IX: one building block of the PBT polymer of diol and acid (molecular weight: 220 g) counts as mol
I: THF formation in stages 1 and 2
II: THF formation during working up
III: BD in the bottom product discharged from C and D
IV: $b_2$ (in): BD in vapors $b_2$
$b_2$ (back): BD recovered from $b_2$
V: $b_1$ (in + back): BD in vapors $b_1$ (completely recovered)
VI: a: BD in vapors a (completely recovered)
VII: all the BD fed into the working up
VIII: total loss of BD in the working up
IX: solid discharged from C and D (0.1 mol of PBT based on 35.2 mol of TPA employed)
*) for comparison

EXAMPLE 2 (FIG. 1)

Stage 1

35.2 mol of dimethyl terephthalate (DMT) and 54.0 mol of BD were reacted in a 3-stage transesterification cascade at 180–205° C. under 1.16 bar absolute. As catalyst, 115 ppm Ti based on PBT were added as TBOT and 0.7 mmol of Na methanolate per kg of PBT at the start of the reaction (residence time τ=205–260 min in total.

The reaction product was transferred with a conversion of at least 95% into stage 2. The precondensation was carried out in the first part of stage 2:

τ=30–40 min,
T=240–290° C.,
P=0.8 bar initially up to 25 mbar.

After the precondensation in stage 2, the product was transferred into the postcondensation in stage 2:

τ=90–140 min,
T=245–265° C.,
P=0.5–2.0 mbar.

The product was then discharged as a melt with a viscosity η (intrinsic) of 0.9–1.3 and was granulated.

The vapors were worked up as depicted in principle in FIG. 1 under the various conditions shown in Table 2.

Working-up variants 2.1. to 2.5. listed in the table were carried out under similar conditions to those listed under 1.1. to 1.5.

As a difference from the working up in Example 1, all the vapors from stage 2 were fed into column B. As a difference from Example 1, MeOH and THF were removed as distillate from columns A and B.

The conditions of pressure, temperature, "Hex", Na and solids content corresponded to Example 1.1 to 1.5.

TABLE 2

Example 2

| Working-up variant | I THF Reaction | II THF Distill. | III BD Discharge C or D | IV b back | IV b in | V a | VI BD working up a + b | VII BD loss in the working up (THF + discharge) | VIII Solid discharge C or D | IX Service life Heat exchangers Columns Pipelines (in days) |
|---|---|---|---|---|---|---|---|---|---|---|
| 2.1. *) | 3.5 | 0.5 | 0.6 | 7.3 | 8.4 | 7.1 | 15.5 | 1.1 | 0.1 | 15–20 |
| 2.2. | 3.5 | <0.1 | 0.3 | 8.1 | 8.4 | 7.1 | 15.5 | 0.3 | 0.1 | 30–200 |
| 2.3. | 3.5 | <0.1 | 0 | 8.4 | 8.4 | 7.1 | 15.5 | <0.1 | 0.1 | 30–150 |

TABLE 2-continued

Example 2

| Working-up variant | I THF Reaction | II THF Distill. | III BD Discharge C or D | IV b back | b in | V a | VI BD working up a + b | VII BD loss in the working up (THF + discharge) | VIII Solid discharge C or D | IX Service life Heat exchangers Columns Pipelines (in days) |
|---|---|---|---|---|---|---|---|---|---|---|
| 2.4. *) | 3.5 | 0.75 | 0.3 | 7.35 | 8.4 | 7.1 | 15.5 | 1.05 | 0.1 | 7–10 |
| 2.5. *) | 3.5 | 0.75 | 1.2 | 6.45 | 8.4 | 7.1 | 15.5 | 1.95 | 0.1 | 7–10 |

I–VIII: all data in mol
VIII: one building block of the PBT polymer of diol and ester (molecular weight: 220 g) counts as mol
I: THF formation in stages 1 and 2
II: THF formation during working up
III: BD in the bottom product discharged from C and D
IV: b (in): BD in vapors b
b (back): BD recovered from b
V: a: BD in vapors a (completely recovered)
VI: all the BD fed into the working up
VII: total loss of BD in the working up
VIII: solid discharged from C and D (0.1 mol of PBT produced per 35.2 mol of DMT employed)
*) for comparison

EXAMPLE 3 (FIG. 3)

The reaction took place as in Example 2 with the difference that all the vapors from stages 1 and 2 were fed into column A. MeOH and THF were removed as distillate from this column. The bottom product was transferred into column C. Further working up took place as in Example 2. The statements concerning "Hex", Na and D apply correspondingly. "Hex" and/or Na methanolate was fed into column A.

As in Examples 1 and 2, 3.4 kg of "Hex" were added per kg of solids and 0.05 kg Na/kg of solids (based on solids in vapors a and b).

The results are to be found in Table 3.

TABLE 3

Example 3

| Working-up variant | I THF Reaction | II THF Distill. | III BD Discharge C or D | IV a back | V b in | VI b + a back | VII a in | VIII BD working up a + b | IX BD loss in working up (THF + discharge) | X Solid discharge C or D | XI Service life Heat exchanger Columns Pipelines (in days) |
|---|---|---|---|---|---|---|---|---|---|---|---|
| 3.1. *) | 3.5 | 0.5 | 3.5 | 12.5 | 8.4 | — | 7.1 | 15.5 | 4.0 | 0.9 | 15–20 |
| 3.2. | 3.5 | <0.1 | 2.3 | 13.2 | 8.4 | — | 7.1 | 15.5 | 2.3 | 0.9 | 30–200 |
| 3.3. | 3.5 | <0.1 | <0.1 | 15.5 | 8.4 | — | 7.1 | 15.5 | <0.1 | 0.9 | 30–150 |
| 3.4. *) | 3.5 | 0.75 | 2.3 | 12.45 | 8.4 | — | 7.1 | 15.5 | 3.05 | 0.9 | 7–10 |
| 3.5. *) | 3.5 | 0.75 | 4.6 | 10.15 | 8.4 | — | 7.1 | 15.5 | 5.35 | 0.9 | 7–10 |

I—X: all data in mol
X: one building block of the PBT polymer of diol and ester (molecular weight: 220 g) counts as mol
I: THF formation in stages 1 and 2
II: THF formation during working up
III: BD in the bottom product discharged from C and D
IV: recovered BD from vapors a and b
V: BD in vapors b
VII: BD in vapors a
VIII: BD fed into the working up
IX: total loss of BD in the working up
X: solids discharged from C and D (0.1 mol of PBT based on 35.2 mol of DMT employed)
*) for comparison

We claim:

1. A process for recovering dihydroxy compounds from residues which result from the preparation of polyesters, which process comprises the steps of esterifying or transesterifying a dicarboxylic acid with a molar excess of a dihydroxy compound in a first stage, wherein an esterification or transesterification product and vapors (a) are formed;

polycondensing the esterification or transesterification product, or a mixture thereof, in at least one second stage, wherein vapors (b), comprising vapors (b1) and vapors (b2), are formed;

transferring vapors (a) and vapors (b1) to at least one first column A;

distilling combined vapors (a) and vapors (b1) in first column A, resulting in low-boiling components as distillate and a bottom product comprising excess dihydroxy compound and oligomeric and polymeric reaction products;

transferring the bottom product from column A to the first stage;

transferring vapors (b2) to at least one second column B;

distilling vapors (b2) in second column B, resulting in low-boiling components as distillate and a bottom product;

transferring the bottom product from second column B to at least one third column C;

distilling the bottom product from second column B in third column C, resulting in dihydroxy compounds and a bottom product;

transferring the bottom product from third column C to an evaporation apparatus D;

removing dihydroxy compound from the bottom product in apparatus D; and returning dihydroxy compound from apparatus D to third column C;

wherein the treatment to recover the dihydroxy compounds is carried out in the presence of an alkali metal or alkaline earth metal compound in an amount of from 0.5 to 10 % by weight, calculated as alkali earth metal or alkaline earth metal, based on the solids content of the vapors.

2. A process for recovering dihydroxy compounds from residues which result from the preparation of polyesters, which process comprises the steps of esterifying or transesterifying a dicarboxylic acid with a molar excess of a dihydroxy compounds in a first stage, wherein an esterification or transesterification product and vapors (a) are formed;

polycondensing the esterification or transesterification product, or a mixture thereof, in at least one second stage, wherein vapors (b) are formed;

transferring vapors (a) to at least one first column A;

distilling vapors (a) in first column A, resulting in low-boiling components as distillate and a bottom product comprising excess dihydroxy compounds and oligomeric and polymeric reaction products;

transferring the bottom product from column A to the first stage;

transferring vapors (b) to at least one second column B;

distilling vapors (b) in second column B, resulting in low-boiling components as distillate and a bottom product;

transferring the bottom product from second column B to at least one third column C;

distilling the bottom product from second column B in third column C, resulting in dihydroxy compounds and a bottom product;

transferring the bottom product from third column C to an evaporation apparatus D;

removing dihydroxy compounds from the bottom product in apparatus D; and returning dihydroxy compounds from apparatus D to third column c;

wherein the treatment to recover dihydroxy compounds is carried out in the presence of an alkali metal or alkaline earth metal compounds in an amount of from 0.5 to 10 % by weight, calculated as alkali earth metal or alkaline earth metal, based on the solids content of the vapors.

3. A process for recovering dihydroxy compounds from residues which result the preparation of polyesters, which process comprises the steps of esterifying or transesterifying a dicarboxylic acid with a molar excess of a dihydroxy compounds in a first stage, wherein an esterification or transesterification product and vapors (a) are formed;

polycondensing the esterification or transesterification product, or a mixture thereof, in at least one second stage, wherein vapors (b) are formed;

transferring vapors (a) and vapors (b) to at least one first column A;

distilling vapors (a) and vapors (b) in first column A, resulting in low-boiling components as distillate and a bottom product comprising excess dihydroxy compounds and oligomeric and polymeric reaction products;

transferring the bottom product from first column A to at least one second column C;

distilling the bottom product from first column A in second column C, resulting in dihydroxy compounds and a bottom product;

transferring the bottom product from second column C to an evaporation apparatus D;

removing dihydroxy compounds from the bottom product in apparatus D; and returning dihydroxy compounds from apparatus D to second column C;

wherein the treatment to recover dihydroxy compounds is carried out in the presence of an alkali metal or alkaline earth metal compounds in an amount of from 0.5 to 10 % by weight, calculated as alkali earth metal or alkaline earth metal, based on the solids content of the vapors.

4. The process of claim 1 wherein the alkali metal compound is an alcoholate.

5. The process of claim 4 wherein the alcoholate is sodium or potassium methanolate, or a mixture thereof.

6. The process of claim 1 wherein the low-boiling component of the vapors comprises a mixture of water or methanol with tetrahydrofuran or acetaldehyde.

7. The process of claim 1 which further comprises the step of adding a liquid residue comprising a dihydroxy compound to the bottom product in column C in a further treatment to recover dihydroxy compounds.

8. The process of claim 1 wherein the temperature in apparatus D is above the melting point of the remaining residue.

9. The process of claim 1 wherein the recovered dihydroxy compound from column C is returned to the first stage.

10. The process of claim 2 wherein the alkali metal compound is an alcoholate.

11. The process of claim 10 wherein the alcoholate is sodium or potassium methanolate, or a mixture thereof.

12. The process of claim 2 wherein the low-boiling component of the vapors comprises a mixture of water or methanol with tetrahydrofuran or acetaldehyde.

13. The process of claim 2 which further comprises the step of adding a liquid residue comprising a dihydroxy compound to the bottom product in column C in a further treatment to recover dihydroxy compounds.

14. The process of claim 2 wherein the temperature in apparatus D is above the melting point of the remaining residue.

15. The process of claim 2 wherein the recovered dihydroxy compound from column C is returned to the first stage of the process.

16. The process of claim 3 wherein the alkali metal compound is an alcoholate.

17. The process of claim 16 wherein the alcoholate is sodium or potassium methanolate, or a mixture thereof.

18. The process of claim 3 wherein the low-boiling component of the vapors comprises a mixture of water of methanol with tetrahydrofuran or acetaldehyde.

19. The process of claim 3 which further comprises the step of adding a liquid residue comprising a dihydroxy compound to the bottom product in column C in a further treatment to recover dihydroxy compounds.

20. The process of claim 3 wherein the temperature in apparatus D is above the melting point of the remaining residue.

21. The process of claim 3 wherein the recovered dihydroxy compound from column C is returned to the first stage of the process.

* * * * *

UNITED STATES PATENT AND TRADEMARK OFFICE
CERTIFICATE OF CORRECTION

PATENT NO.   : 6,174,970 B1
DATED        : January 16, 2001
INVENTOR(S)  : Peter Braune It is certified that error appears in the above-identified patent and that said Letters Patent is hereby corrected as shown below:

Column 12,
Line 11, "column c" should be -- column C --.
Line 18, after "result" insert -- from --.

Signed and Sealed this

Tenth Day of August, 2004

JON W. DUDAS
*Acting Director of the United States Patent and Trademark Office*